United States Patent
Olek (10) Patent No.: US 11,788,141 B2
(45) Date of Patent: Oct. 17, 2023

(54) MVD AS EPIGENETIC MARKER FOR THE IDENTIFICATION OF IMMUNE CELLS, IN PARTICULAR CD56+ NK CELLS

(71) Applicant: Precision for Medicine Gmbh, Berlin (DE)

(72) Inventor: Sven Olek, Berlin (DE)

(73) Assignee: Precision for Medicine GmbH, Berlin (DE)

( * ) Notice: Subject to any disclaimer, the term of this patent is extended or adjusted under 35 U.S.C. 154(b) by 0 days.

(21) Appl. No.: 15/752,048

(22) PCT Filed: Sep. 22, 2016

(86) PCT No.: PCT/EP2016/072522
§ 371 (c)(1),
(2) Date: Feb. 12, 2018

(87) PCT Pub. No.: WO2017/050882
PCT Pub. Date: Mar. 30, 2017

(65) Prior Publication Data
US 2018/0237855 A1    Aug. 23, 2018

(30) Foreign Application Priority Data
Sep. 25, 2015  (GB) ..................... 1516971

(51) Int. Cl.
*C12Q 1/6881* (2018.01)
*A61K 35/17* (2015.01)

(52) U.S. Cl.
CPC ............ *C12Q 1/6881* (2013.01); *A61K 35/17* (2013.01); *C12Q 2600/118* (2013.01); *C12Q 2600/142* (2013.01); *C12Q 2600/154* (2013.01); *C12Q 2600/158* (2013.01)

(58) Field of Classification Search
CPC ............ C12Q 1/6881; C12Q 2600/118; C12Q 2600/142; C12Q 2600/154; C12Q 2600/158; A61K 35/17
See application file for complete search history.

(56) References Cited

U.S. PATENT DOCUMENTS

| 2007/0269823 A1* | 11/2007 | Huehn ................ C12Q 1/6886 435/6.16 |
| --- | --- | --- |
| 2013/0129668 A1 | 5/2013 | Firestein et al. |
| 2013/0260378 A1* | 10/2013 | Olek ........................ C12Q 1/68 435/6.11 |

FOREIGN PATENT DOCUMENTS

| WO | 2010125106 A1 | 11/2010 |
| --- | --- | --- |
| WO | 2013014122 A1 | 1/2013 |

OTHER PUBLICATIONS

Zhang (eLife (2015) vol. 4, pp. 1-16).*
May et al (Science (1988) vol. 241, p. 1441).*
Benner et al (Trends in Genetics (2001) vol. 17, pp. 414-418).*
Ehrlich et al. (2002 Oncogene vol. 21 p. 5400).*
Walsh et al teaches (Genes & Development (1999) vol. 13, pp. 26-36).*
Brooks et al (Cancers Causes control (2009) vol. 20, pp. 1539-1550).*
Ushijima (Nature Reviews. 2005. 5: 223-231).*
Sabbioni et al (Mol Diagn 7(3):201-207 [2003]).*
Zhang (PLOS Genetics (2009) vol. 5, e1000438).*
Pompeia (Cancer Genomics & Proteomics (2004) vol. 1, pp. 387-406).*
Kristen (Clinical Chemistry (2009) vol. 55, pp. 1471-1483).*
Harrison (Frontiers in Genetics (2011) vol. 2, article 74, pp. 1-13).*
Dahl (Biogerontology (2003) vol. 4, pp. 233-250).*
Blast ® » blastn suite » results for RID-YUUNEMKP01R (NCBI Blast:Nucleotide Sequence (nih.gov), downloaded Jan. 23, 2022).*
GenBank: AC116552.2 *Homo sapiens* chromosome 16 clone RP11-21B21, complete sequence (PRI 07-Jan. 2004, *Homo sapiens* chromosome 16 clone RP11-21B21, complete sequence—Nucleotide—NCBI (nih.gov)).*
Schroeder (Proceedings National Academy of Sciences (2013) vol. 110, pp. 6037-6042).*
Li (Thesis: Modulating the Expression of Enzymes of Isoprenoid Synthesis: Effects on Vγ9Vδ2 T Cell Activation and Tumor Cell Growth (2009).*
Gruenbacher(Cancer Res; 70(23); 9611-20.(2010).*
Schroeder (Proceedings National Academy of Sciences (2013) vol. 110, pp. 6037-6042+ supplemental data).*
Baron, U. et al., "DNA Methylation Analysis as a Tool for Cell Typing." Epigenetics, 2006, 1 (1): 55-59.
Michihara, A. et al., "Comparison of the Gene Expression Levels of Mevalonate Pyrophosphate Decarbocylase between Stroke-prone Spontaneously Hhypertensive and Wistar Kyoto Rats." Journal of Health Science, 2010, 56 (6): 733-737.
Shi, J. et al., "Mevalonate pathway is a therapeutic target in esophageal squamous cell carcinoma." Tumor. Biol., 2013, 34(1): 429-435.

* cited by examiner

*Primary Examiner* — Steven Pohnert
(74) *Attorney, Agent, or Firm* — BakerHostetler (57) ABSTRACT

The present invention relates to a method, in particular an in vitro method, for identifying CD56+ NK cells, comprising analyzing the methylation status of at least one CpG position in the mammalian gene region for mevalonate (diphospho) decarboxylase (MVD), wherein a demethylation or lack of methylation of said gene region is indicative for a CD56+ NK cell, when compared to a non-CD56+ NK cell. The analyses according to the invention can identify CD56+ NK cells on an epigenetic level and distinguish them from all other cells in complex samples, such as, for example, other blood or immune cells. The present invention furthermore provides an improved method for quantifying CD56+ NK cells, in particular in complex samples. The method can be performed without a step of purifying and/or enriching cells, preferably in whole blood and/or non-trypsinized tissue.

18 Claims, 2 Drawing Sheets

Specification includes a Sequence Listing.

SEQUENCE LISTING

```
<160> NUMBER OF SEQ ID NOS: 11

<210> SEQ ID NO 1
<211> LENGTH: 439
<212> TYPE: DNA
<213> ORGANISM: Homo sapiens

<400> SEQUENCE: 1
ggtgtgggtc tgagtccacc ccacagggca ggccctgac cattagaagg tgttattgct      60
cccacccggg acagacgcac atccccacac gcttccagac acccttaaat gggaggcgcc    120
tctcacattg agaataagac accatgaaaa cacgggaggg aagaaatcaa cagccccggg    180
gcgtaaggag gctgggccaa gctgtgcacc gaggagggcg tacatggggg ctctgtggca    240
cccccacaga gcagcgcagg ggaagaggcg gttcagggcc aagctgtgca ccgaggaggg    300
cgtacatggg ggctctgtgg cgccaagatg cagctgccgg accccaccca agaaaagaca    360
cccaactgcc ggggcggggt caacacccgg ccgccttgac tggctctaac tcgcttcagt    420
aagaaggaaa tcaggggct                                                  439

<210> SEQ ID NO 2
<211> LENGTH: 439
<212> TYPE: DNA
<213> ORGANISM: Homo sapiens

<400> SEQUENCE: 2
ggtgtgggtt tgagtttatt ttatagggta ggttttttgat tattagaagg tgttattgtt     60
tttatttggg atagatgtat attttttatat gtttttagat attttttaaat gggaggtgtt   120 ttttatattg agaataagat attatgaaaa tatgggaggg aagaaattaa tagttttggg    180
gtgtaaggag gttgggttaa gttgtgtatt gaggagggtg tatatggggg ttttgtggta    240
tttttataga gtagtgtagg ggaagaggtg gtttagggtt aagttgtgta ttgaggaggg    300
tgtatatggg ggttttgtgg tgttaagatg tagttgttgg attttatttta agaaaagata    360
```
tttaattgtt ggggtggggt taatatttgg ttgttttgat tggttttaat ttgttttagt    420
aagaaggaaa ttaggggtt    439

<210> SEQ ID NO 3
<211> LENGTH: 439
<212> TYPE: DNA
<213> ORGANISM: Homo sapiens

<400> SEQUENCE: 3
ggtgtgggtt tgagtttatt ttatagggta ggttttgat tattagaagg tgttattgtt    60
tttattcggg atagacgtat attttttatac gttttttagat attttttaaat gggaggcgtt    120 ttttatattg agaataagat attatgaaaa tacgggaggg aagaaattaa tagtttcggg    180
gcgtaaggag gttgggttaa gttgtgtatc gaggagggcg tatatggggg ttttgtggta    240
tttttataga gtagcgtagg ggaagaggcg gtttagggtt aagttgtgta tcgaggaggg    300
cgtatatggg ggttttgtgg cgttaagatg tagttgtcgg attttatta agaaaagata    360 tttaattgtc gggcggggt taatattcgg tcgttttgat tggttttaat tcgttttagt    420
aagaaggaaa ttaggggtt    439

<210> SEQ ID NO 4
<211> LENGTH: 21
<212> TYPE: DNA
<213> ORGANISM: Homo sapiens

<400> SEQUENCE: 4
ggtgtgggtt tgagtttatt t    21

<210> SEQ ID NO 5
<211> LENGTH: 22
<212> TYPE: DNA
<213> ORGANISM: Homo sapiens

<400> SEQUENCE: 5 aaccccctaat ttccttctta ct    22

<210> SEQ ID NO 6
<211> LENGTH: 26
<212> TYPE: DNA
<213> ORGANISM: Homo sapiens

<400> SEQUENCE: 6
gttttgtggt atttttatag agtagt    26

<210> SEQ ID NO 7
<211> LENGTH: 20
<212> TYPE: DNA
<213> ORGANISM: Homo sapiens

<400> SEQUENCE: 7
agatgggatg gaatggttgt    20

<210> SEQ ID NO 8
<211> LENGTH: 23
<212> TYPE: DNA
<213> ORGANISM: Homo sapiens

<400> SEQUENCE: 8
cctaaaccac ctcttcccct aca    23

```
<210> SEQ ID NO 9
<211> LENGTH: 25
<212> TYPE: DNA
<213> ORGANISM: Homo sapiens

<400> SEQUENCE: 9
ttttgtggta tttttataga gtagc                                   25

<210> SEQ ID NO 10
<211> LENGTH: 18
<212> TYPE: DNA
<213> ORGANISM: Homo sapiens

<400> SEQUENCE: 10
ccatatacgc cctcctcg                                           18

<210> SEQ ID NO 11
<211> LENGTH: 20
<212> TYPE: DNA
<213> ORGANISM: Homo sapiens

<400> SEQUENCE: 11
aaaccgcctc ttcccctacg                                         20
```

MVD AS EPIGENETIC MARKER FOR THE IDENTIFICATION OF IMMUNE CELLS, IN PARTICULAR CD56+ NK CELLS

CROSS REFERENCE TO RELATED APPLICATIONS

This application is a National Stage Application of International Application Number PCT/EP2016/072522, filed Sep. 22, 2016; which claims priority to Great Britain Patent Application No. 1516971.7, filed Sep. 25, 2015.

The Sequence Listing for this application is labeled "SeqList-12Feb18-ST25.txt", which was created on Feb. 12, 2018, and is 4 KB. The entire content is incorporated herein by reference in its entirety.

The present invention relates to a method, in particular an in vitro method, for identifying cluster differentiation 56+ (CD56+) natural killers (NK) cells, comprising analyzing the methylation status of at least one cytosine-phosphodiester-guanine (CpG) position in the mammalian gene region for mevalonate (diphospho) decarboxylase (MVD), wherein a demethylation or lack of methylation of said gene region is indicative for a CD56+ NK cell, when compared to a non-NK cell. The analyses according to the invention can identify CD56+ NK cells on an epigenetic level and distinguish them from all other cells in complex samples, such as, for example, other blood or immune cells. The present invention furthermore provides an improved method for quantifying CD56+ NK cells, in particular in complex samples. The method can be performed without a step of purifying and/or enriching cells, preferably in whole blood and/or non-trypsinized tissue.

Furthermore, the present invention relates to a kit for performing the above methods as well as respective uses thereof. It is one aim of this invention to provide a novel, more robust means to quantitatively detect and measure CD56+ NK cells of the blood within any solid organs or tissue or any body fluid of a mammal.

BACKGROUND OF THE INVENTION

Natural killer cells or NK cells are a type of cytotoxic lymphocyte critical to the innate immune system. The role NK cells play is analogous to that of cytotoxic T cells in the vertebrate adaptive immune response. NKs express the NCAM-1 molecule, which clusterises as CD56. Another classical marker of NK cells, is the FcγRIII also called CD16. NK cells can be subdivided into different populations based on the relative expression of the surface markers CD16 and CD56. The two major subsets are $CD_{56}^{bright}$ $CD16^{dim/-}$ and $CD56^{dim}CD16^{+}$, respectively. In blood, there are at least two lymphocytes populations that express CD56 as NK cells, including cells that are CD3+, i.e. a group of cells that express NK markers and T cell markers, sometimes called NKT cells. CD3+CD56+ cells represent one of the other NK T cell populations.

Even though almost all cells in an individual contain the exact same complement of DNA code, higher organisms must impose and maintain different patterns of gene expression in the various types of tissue. Most gene regulation is transitory, depending on the current state of the cell and changes in external stimuli. Persistent regulation, on the other hand, is a primary role of epigenetics—heritable regulatory patterns that do not alter the basic genetic coding of the DNA. DNA methylation is the archetypical form of epigenetic regulation; it serves as the stable memory for cells and performs a crucial role in maintaining the long-term identity of various cell types. Recently, other forms of epigenetic regulation were discovered. In addition to the "fifth base" 5-methylcytosine (mC), a sixth (5-hydroxymethylcytosine, hmC), seventh (5-formylcytosine, fC) and eighth (5-carboxycytosine, cC) can be found (Michael J. Booth et al. Quantitative Sequencing of 5-Methylcytosine and 5-Hydroxymethylcytosine at Single-Base Resolution Science 18 May 2012, Vol. 336 no. 6083 pp. 934-937).

The primary target of mentioned DNA modifications is the two-nucleotide sequence Cytosine-Guanine (a 'CpG site'); within this context cytosine (C) can undergo a simple chemical modification to become formylated, methylated, hydroxymethylated, or carboxylated. In the human genome, the CG sequence is much rarer than expected, except in certain relatively dense clusters called 'CpG islands'. CpG islands are frequently associated with gene promoters, and it has been estimated that more than half of the human genes have CpG islands (Antequera and Bird, Proc Natl Acad Sci USA 90: 11995-9, 1993).

Aberrant methylation of DNA is frequently associated with the transformation from healthy to cancerous cells. Among the observed effects are genome-wide hypomethylation, increased methylation of tumor suppressor genes, and hypomethylation of many oncogenes (reviewed, for example, by Jones and Laird, Nature Genetics 21:163-167, 1999; Esteller, Oncogene 21:5427-5440, 2002; and Laird, Nature Reviews/Cancer 3:253-266, 2003). Methylation profiles have been recognized to be tumor specific (i.e., changes in the methylation pattern of particular genes or even individual CpGs are diagnostic of particular tumor types), and there is now an extensive collection of diagnostic markers for bladder, breast, colon, esophagus, stomach, liver, lung, and prostate cancers (summarized, for example, by Laird, Nature Reviews/Cancer 3:253-266, 2003).

For one of the recently described modification of cytosine, 5-hydroxymethylation, the utility of oxidative bisulfite sequencing to map and quantify 5hmC at CpG islands was shown (Michael J. Booth et al. Quantitative Sequencing of 5-Methylcytosine and 5-Hydroxymethylcytosine at Single-Base Resolution Science 18 May 2012, Vol. 336 no. 6083 pp. 934-937). High levels of 5hmC were found in CpG islands associated with transcriptional regulators and in long interspersed nuclear elements. It is suggested that these regions might undergo epigenetic reprogramming in embryonic stem cells.

WO 2012/162660 describes methods using DNA methylation arrays are provided for identifying a cell or mixture of cells and for quantification of alterations in distribution of cells in blood or in tissues, and for diagnosing, prognosing and treating disease conditions, particularly cancer. The methods use fresh and archival samples.

WO 2013/014122 relates to a method, in particular an in vitro method for identifying natural killer cells and their subgroups in a mammal, preferably CD3 negative, non T-lymphocyte derived NK cells, which often express the surface proteins CD56 and/or CD 16, comprising analyzing the accessibility of the genomic DNA for OSBPL, such as OSBPL5, to bisulfite conversion and/or the methylation status of at least one CpG position in the genes for OSBPL, such as OSBPL5.

Accomando et al. (in: Accomando et al. Decreased NK cells in patients with head and neck cancer determined in archival DNA. *Clinical Cancer Research* 2012; 18(22): 6147-6154) disclose that NK cell-specific DNA methylation was identified by analyzing DNA methylation and mRNA array data from purified blood leukocyte subtypes (NK, T, B, monocytes, granulocytes), and confirmed via pyrosequencing and quantitative methylation specific PCR (qMSP). NK cell levels in archived whole blood DNA from 122 HNSCC patients and 122 controls were assessed by qMSP. Pyrosequencing and qMSP confirmed that a demethylated DNA region in NKp46 distinguishes NK cells from other leukocytes, and serves as a quantitative NK cell marker.

In view of the above, it is an object of the present invention to provide an improved and in particular robust method based on DNA-methylation analysis as a superior tool in order to more conveniently and reliably detect, identify, discriminate, and quantify CD56+ NK cells.

The present invention solves the above object by providing method for identifying CD56+NK cells in a sample, comprising analyzing the methylation status (bisulfite convertibility) of at least one CpG position in the mammalian (e.g. human) gene region for mevalonate (diphospho) decarboxylase (MVD), wherein preferably said gene region as analyzed is positioned based on/according to SEQ ID NO: 1, wherein a demethylation of said gene region is indicative for a CD56+ NK cell, when compared to a non-CD56+ NK cell.

The protein mevalonate (diphospho) decarboxylase (MVD, or MPD) is part of the mevalonate pathway that provides metabolites for post-translational modifications such as farnesylation, which are critical for the activity of RAS downstream signaling. No phenotype or disease is known to be directly associated with this gene. The gene for human MVD is found on chromosome 16: 88,651,935-88, 663,161 reverse strand; Ensembl-ID: ENSG00000167508

In the context of the present invention, the gene region shall comprise all of the genomic region relating to and encoding for MVD. Thus, included are enhancer regions, promoter region(s), introns, exons, and non-coding regions (5'- and/or 3'-regions) that belong to MVD. Preferred is thus a method according to the present invention, wherein the at least one CpG position is present in the 5' region upstream from the transcription start, promoter region, the 5' or 3' untranslated regions, exon, intron, exon/intron border and/or in the 3' region downstream of the transcriptional stop of the gene as analyzed.

The present invention is further based on the surprising identification of a region of the MVD gene by the inventors, as specific epigenetic marker, allowing the identification of CD56+ NK cells as well as the clinical routine application of said analysis.

In the context of the present invention, the genomic region of MVD, in particular according to SEQ ID NO: 1 allows the identification of CD56+ NK cells. Surprisingly, the discriminatory pattern of bisulfite convertible and non-convertible cytosine is particularly and even exclusively limited to the genomic region according to SEQ ID NO: 1 for CD56+ NK cells as shown using the amplicon according to SEQ ID NO: 1, and in particular in the bisulfite converted sequences according to SEQ ID NO: 2 and/or SEQ ID NO: 3.

The inventors could demonstrate that in the CD56+ NK cells the CpG motifs as disclosed are almost completely demethylated (i.e. to more than 70%, preferably 80%, preferably, more than 90% and most preferred more than 95%), whereas the same motifs are completely methylated in all other immune cells.

The differential methylation of the CpG motifs within the aforementioned regions is a valuable tool to identify CD56+ NK cells, such as will be required/or at least of some value for identifying and quantifying said cells in autoimmune diseases, transplant rejections, cancer, allergy, primary and secondary immunodeficiencies, such as, for example, HIV infections and AIDS, Graft versus Host (GvH), hematologic malignancies, rheumatoid arthritis, multiple sclerosis, or a cytotoxic T cell related immune status in any envisionable diagnostic context. The assay allows measurement of CD56+ NK cells without purification or any staining procedures.

Another preferred aspect of the method according to the present invention then further comprises a quantification of the relative amount of CD56+ NK cells based on comparing relative amounts of said methylation frequency in the region as analyzed with relative amounts of the methylation frequency in a control gene, such as, for example, human glyceraldehyde 3-phosphate dehydrogenase (GAPDH). Said quantification is thus achieved based on the ratio of the bisulfite convertible DNA to non-convertible DNA in the genetic region of MVD (e.g. of SEQ ID NO: 1) as described and analyzed herein. Most preferred is a quantification of the relative amount of CD56+ NK cells is based on an (preferably parallel or simultaneous) analysis of the relative amount of bisulfite convertible DNA of cell-specific region for MVD, and of the relative amount of bisulfite convertible DNA of cell-unspecific genes (preferably designated "control genes" or "control regions", such as, for example, the gene for GAPDH).

In a further preferred embodiment of the method according to the present invention, said analysis of bisulfite convertibility comprises amplification with at least one primer of suitable primer pairs that can be suitably designed based on SEQ ID NO: 1, preferably oligomers according to any of SEQ ID NO: 2 to SEQ ID NO: 4.

In contrast to FACS and mRNA measurements, using the methods according to the present invention, the measurement(s) and analyses can be done independent of purification, storage—and to quite some extent—also to tissue quality.

Preferably, the amplification involves a polymerase enzyme, a PCR or chemical amplification reaction, or other amplification methods as known to the person of skill as described below, e.g. in the context of methylation-specific PCR (MSP), HEAVYMETHYL™, SCORPION™, methylation-sensitive single-nucleotide primer extension (MS-SNuPE), METHYLLIGHT™ bisulfite sequencing, methyl specific restriction assays and/or digital PCR (see, for example Kristensen and Hansen PCR-Based Methods for Detecting Single-Locus DNA Methylation Biomarkers in Cancer Diagnostics, Prognostics, and Response to Treatment Clinical Chemistry 55:8 1471-1483 (2009)).

With the amplification, an amplicon of the MVD gene region is produced that is a particularly preferred "tool" for performing the method(s) according to the present invention. Consequently, oligomers according to any of SEQ ID NOs: 4 and 5 or an amplicon as amplified by a primer pair based on SEQ ID NOs: 4 and 5 or SEQ ID NOs: 6 and 7 or SEQ ID NOs: 9 and 10 as mentioned herein constitute preferred embodiments of the present invention. Thus, the sequences of SEQ ID NOs: 1 to 3 (and, if needed, the complementary sequences thereto) can be used to design primers for amplifications, i.e. serve as "beacons" in the sequence as relevant. Similarly, additional primers and probes can be designed based on the amplicon according to SEQ ID NO: 1. Amplification can take place either in the genomic and/or bisulfite (i.e. "converted") DNA sequence.

The person of skill will furthermore be able to select specific subsets of CpG positions in order to minimize the amount of sites to be analyzed, for example at least one of CpG position selected from a CpG position in an amplicon according to SEQ ID NO: 1, and is preferably selected from CpG positions 1, 2, 3, 4, 5, 6, 7, 8, 9, 10, 11, 12, 13, 14, 15, 16, 17, 18, 19, and 20 in the amplicon No. 2674 according to SEQ ID NO: 1. The positions are numerically counted from the 5'-end of an amplicon as generated and analyzed, and are designated as 67, 76, 90, 117, 153, 177, 182, 210, 219, 255, 269, 292, 301, 321, 338, 370, 375, 388, 392, and 412 in FIG. 1. Preferred are combinations of 3, 4, 5, 6, 7, 8, 9, or 10 positions, the analysis of which produces sufficient data and/or information in order to be informative in the context of the present invention.

The person of skill will furthermore be able to select specific subsets of CpG positions in order to minimize the amount of sites to be analyzed, for example at least one of CpG position 10, 11, 12, and/or 13 in the amplicon No. 2674 of the MVD specific bisulfite convertible region (SEQ ID NO: 1), or all sites as present on the bisulfite convertible region according to SEQ ID NO: 1. One or more of positions 153, 321, and/or 388 may be excluded.

In order to analyze the bisulfite convertibility of CpG positions, any known method to analyze DNA methylation can be used. In a preferred embodiment of the method according to the present invention, the analysis of the methylation status comprises a method selected from methylation specific enzymatic digests, bisulphite sequencing, analysis selected from promoter methylation, CpG island methylation, methylation-specific PCR (MSP), HEAVYMETHYL™, METHYLLIGHT™, methylation-sensitive single-nucleotide primer extension (MS-SNuPE), or other methods relying on a detection of amplified DNA. These methods are well known to the person of skill, and can be found in the respective literature.

In a preferred embodiment of the method according to the present invention, said method is suitable for routine application, for example on a DNA-chip. Based on the above information and the respective literature, the person of skill will be able to adjust the method as above to such settings.

In yet another preferred embodiment of the methods according to the present invention, said method is performed without a step of purifying and/or enriching said cells to be identified, preferably using whole blood and/or non-trypsinized tissue.

In another preferred embodiment of the method according to the present invention, the identification comprises a distinction of said CD56+ NK cells from all major peripheral blood cell types and/or non-blood cells, preferably, but not limited to, from follicular helper T cells, cytotoxic T-cells, granulocytes, monocytes, B-cells, CD56++ ("bright") NK cells, and T-helper cells, and optionally NKT cells, and other cell types derived from other organs than blood.

In yet another preferred embodiment of the method according to the present invention, the sample is selected from a mammalian body fluid, including human blood samples, or a tissue, organ or a sample of leukocytes or a purified or separated fraction of such tissue, organ or leukocytes or a cell type sample. Preferably, said mammal is a mouse, goat, dog, pig, cat, cow rat, monkey or human. The samples can be suitably pooled, if required.

Another preferred aspect of the method according to the present invention then further comprises the step of concluding on the immune status of said mammal based on said B cells. The B cells can be quantified and be used as a benchmark to relatively quantify further detailed subpopulations, or it can be used as a predictive and/or screening and/or diagnostic and/or prognostic and/or adverse events detecting factor, or it can be used to finally detect this population to determine the overall immune activity status.

In yet another preferred embodiment of the methods according to the present invention, the mammal suffers from or is likely to suffer from autoimmune diseases, transplant rejections, infection diseases, cancer, and/or allergy as but not limited to Trypanosoma cruzi-infection, Malaria and HIV infection; Hematologic Malignancies as but not limited to chronic Myelogenous Leukemia, Multiple Myeloma, Non Hodgkin's Lymphoma, Hodgkin's Disease, chronic Lymphocytic Leukemia, Graft versus Host and Host versus Graft Disease, Mycosis fungoides, Extranodal T cell lymphoma, Cutaneous T cell lymphomas, Anaplastic large cell lymphoma, Angioimmunoblastic T cell lymphoma and other T-cell, B-cell and NK cell neoplasms, T cell deficiencies such as but not limited to lymphocytopenia, severe combined immunodeficiency (SCID), Omenn syndrome, Cartilage-hair hypoplasia, acquired immune deficiency syndrome (AIDS), and hereditary conditions such as DiGeorge syndrome (DGS), chromosomal breakage syndromes (CBSs), multiple sclerosis, rheumatoid arthritis, systemic lupus erythematosus, Sjögren's syndrome, systemic sclerosis, dermatomyositis, primary biliary cirrhosis, primary sclerosing cholangitis, ulcerative colitis, Crohn's disease, psoriasis, vitiligo, bullous pemphigoid, alopecia areata, idiopathic dilated cardiomyopathy, type 1 diabetes mellitus, Graves' disease, Hashimoto's thyroiditis, myasthenia gravis, IgA nephropathy, membranous nephropathy, and pernicious anemia; and B-cell and T-cell combined disorders such as but not limited to ataxia telangiectasia (AT) and Wiskott-Aldrich syndrome (WAS); and carcinomas such as but not limited to breast cancer, colorectal cancer, gastric cancer, pancreatic cancer, hepatocellular carcinoma, cholangiocarcinoma, melanoma, and head and neck cancer.

Another preferred aspect of the method according to the present invention then relates to a method as above, further comprising measuring and/or monitoring the amount of CD56+ NK cells in response to chemical and/or biological substances that are provided to said mammal, i.e. in response to a treatment of said patient. Said method comprises the steps as above, and comparing said relative amount of said cells as identified to a sample taken earlier or in parallel from the same mammal, and/or to a control sample. Based on the results as provided by the method(s) of the invention, the attending physician will be able to conclude on the immune status of the patient, and adjust a treatment of the underlying disease accordingly.

Preferably, said method is performed without a step of purifying and/or enriching cells, preferably in whole blood and/or non-trypsinized tissue, or any other biological sample potentially containing said CD56+ NK cells as e.g. a sample for cell transfer into a patient.

Another preferred aspect of the method according to the present invention then relates to a method as above, further comprising formulating said CD56+ NK cells as identified for transplantation into a patient. Pharmaceutical preparations for these purposes and methods for their production are performed according to methods known in the art of transplantation medicine.

Another preferred aspect of the method according to the present invention relates to an oligomer according to any of SEQ ID NOs: 4 to 11, or an amplicon according to SEQ ID NOs: 1 to 3.

Yet another preferred aspect of the present invention then relates to a kit for identifying, quantifying, and/or monitoring CD56+ NK cells in a mammal based on the analysis of the bisulfite accessibility of CpG positions in the gene region of MVD, comprising components for performing a method according to invention as described herein, in particular a kit comprising a) a bisulfite reagent, and b) materials for the analysis of the methylation status of CpG positions selected from the CpG positions in the region according to SEQ ID NO: 1, such as an oligomer selected from the sequences according to SEQ ID NOs: 4 to 11.

The present invention also encompasses the use of oligomers or amplicon or a kit according to the present invention for identifying and/or for monitoring CD56+ NK cells in a mammal as described herein.

As mentioned above, recently three new cytosine modifications were discovered. Therefore, it is expected that future scientific findings will correct epigenetic patterns of modification described in the past. These past patterns of cytosine modification encompass bisulfite convertible (non-methylated, non-modified) and non-convertible (methylated, modified) cytosine. Both termini need to be corrected, as described. According to the novel scientific findings (i) non-bisulfite convertible cytosine encompasses 5-methylcytosine (mC) and 5-hydroxymethylcytosine (hmC), and (ii) bisulfite convertible (i.e. the "bisulfite convertibility") cytosine encompasses 5-formylcytosine (fC), 5-carboxycytosine (cC), as well as non-modified cytosine.

Additionally, past inventions are based on (i) the ratio of bisulfite convertible cytosine to whole amount of chromatin (cell-type independent, 100% bisulfite convertible DNA locus) or (ii) on the ratio of bisulfite convertible cytosine (fC, cC, non-modified cytosine) to non-bisulfite convertible cytosine (hmC and mC). These ratios characterize cell type, cell differentiation, cell stage as well as pathological cell stages. Therefore, new techniques will result in novel, more specific ratios and might supplement current cell specific, cell state specific as well as pathological patterns of epigenetic modifications and therefore, define potential novel biomarkers. Novel ratios to be discovered as biomarkers can be defined as:

Biomarker Ratio=$a/b$ $a=\Sigma(C$ and/or $mC$ and/or $hmC$ and/or $fC$ and/or $cC)$ $b=\Sigma(C$ and/or $mC$ and/or $hmC$ and/or $fC$ and/or $cC)$, whereby a and b differs from each other by one to four kinds of modifications. Discovery of novel DNA modifications will enlarge this enumeration.

For the purpose of definition for the present application, "epigenetic modifications" in the DNA sequence is referred to by the terminology of (i) bisulfite convertible cytosine (5-formylcytosine, (fC) and/or 5-carboxycytosine (cC)) and (ii) non-bisulfite convertible cytosine ((including 5-methylcytosine (mC), 5-hydroxymethylcytosine, (hmC)). As both kinds of methylation, mC and hmC, are not bisulfite convertible, it is not possible to distinguish between these two. Likewise, fC, cC as well as non-modified cytosine are bisulfite convertible and can also not be distinguished from each other as well. The term "methylated" DNA encompasses mC as well as hmC. The term "non-methylated" DNA encompasses fC, cC, and non-modified DNA. It is expected that novel variants of DNA modifications will be discovered in future. Each type of modification will be either bisulfite convertible or not. However, since the present method reliably distinguishes between the two groups, these novel modifications will also be usable as markers.

Furthermore, apart from the modifications of DNA, also histones undergo posttranslational modifications that alter their interaction with DNA and nuclear proteins. Modifications include methylation, acetylation, phosphorylation, ubiquitination, sumoylation, citrullination, and ADP-ribosylation. The core of the histones H2A, H2B, and H3 can also be modified. Histone modifications act in diverse biological processes such as gene regulation, DNA repair, chromosome condensation (mitosis) and spermatogenesis (meiosis). Also for these modifications a specific pattern of modification is specific for different cell types, cell stages, differentiation status and such a pattern can be analyzed for bisulfite convertibility or similar methods in order to identify certain cells and cell stages. The present invention also encompasses a use of these modifications.

In summary, using the MVD genetic region and in particular the amplicon as described herein as a marker, the inventors very specifically identified, quantified and particularly differentiated CD56+ NK cells, and in their relation to other cell types in a sample, for example to other blood cells.

The invention will now be further described based on the following examples and with reference to the accompanying figures and the sequence listing, without being limited thereto. For the purposes of the present invention, all references as cited herein are incorporated by reference in their entireties.

BRIEF DESCRIPTION OF THE DRAWINGS

FIG. 2, parts A and B, are a series of graphs depicting the TpG-specific PCR-system using plasmid-DNA test-template (A) and the CpG-specific PCR-system using plasmid-DNA test-template (B).

SEQ ID NO: 1 shows the genomic sequence of amplicon AMP2674 according to the present invention.

SEQ ID NOs: 2 and 3 show the sequences of bisulfite-converted target-regions of preferred qPCR-assay-systems of the invention.

SEQ ID NOs: 4 to 11 show the sequences of specific oligomers (primers and probes) according to the present invention.

EXAMPLES

Example 1

In order to identify CD56+ NK cells, qPCR was performed on bisulphite converted samples stemming from the human genomic region according to the following sequence (AMP2674, SEQ ID NO: 1), relevant CpGs are shaded in gray:

```
GGTGTGGGTCTGAGTCCACCCCACAGGGCAGGCCCCTGACCATTAGAAGGTGTTATTGCTCCCACCCGGGACAGA

CGCACATCCCCACACGCTTCCAGACACCCTTAAATGGGAGGCGCCTCTCACATTGAGAATAAGACACCATGAAAA

CACGGGAGGGAAGAAATCAACAGCCCCGGGGCGTAAGGAGGCTGGGCCAAGCTGTGCACCGAGGAGGGCGTACAT

GGGGGCTCTGTGGCACCCCACAGAGCAGCGCAGGGGAAGAGGCGGTTCAGGGCCAAGCTGTGCACCGAGGAGGG

CGTACATGGGGGCTCTGTGGCGCCAAGATGCAGCTGCCGGACCCCACCCAAGAAAAGACACCCAACTGCCGGGGC

GGGGTCAACACCCGGCCGCCTTGACTGGCTCTAACTCGCTTCAGTAAGAAGGAAATCAGGGGCT
```

Figure 1:
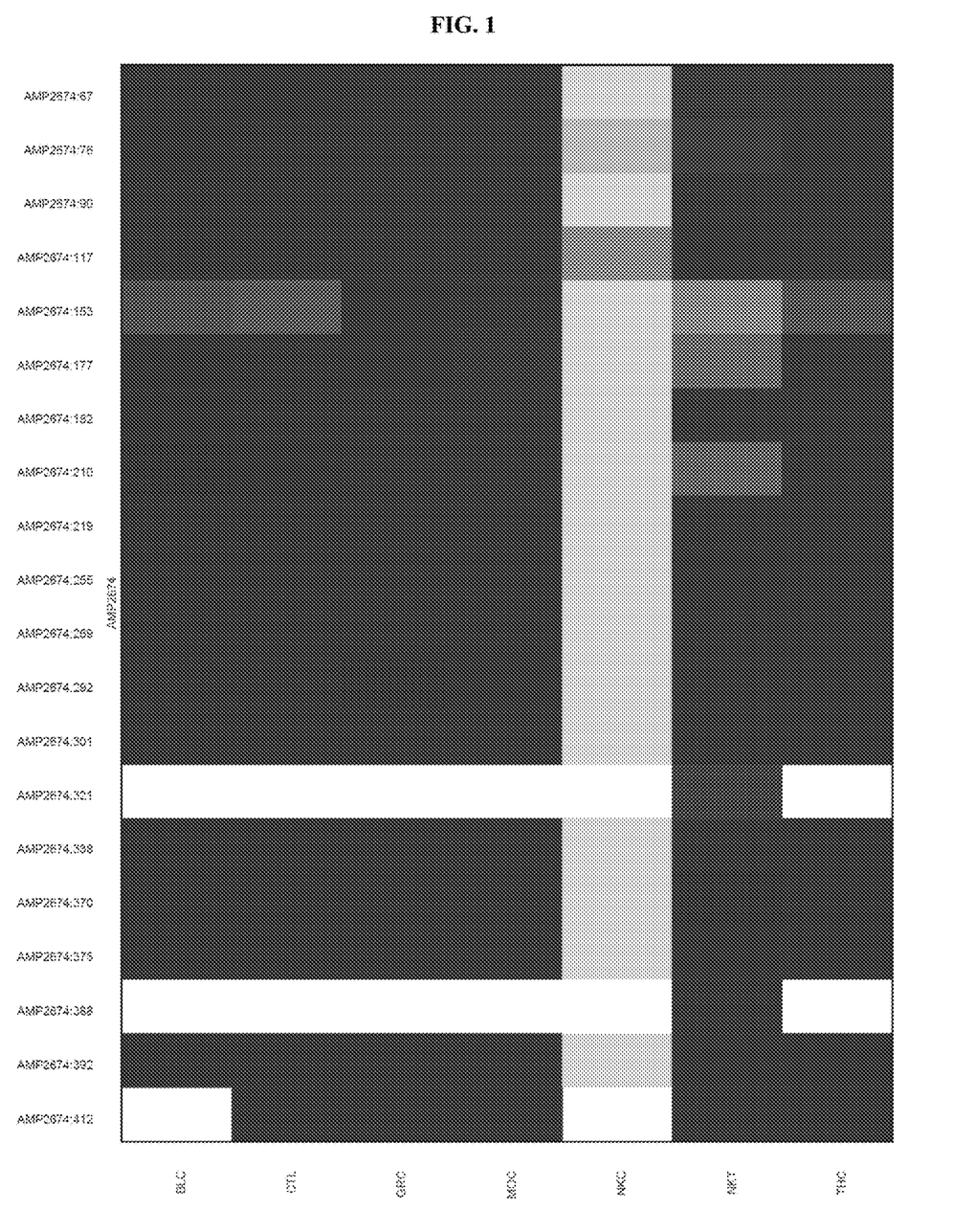
FIG. 1 shows the analysis of CpG sites on amplicon No. 2674 (SEQ ID NO: 1) according to the invention. The horizontal boxes in the table correspond to the CpG positions in the amplicon as analyzed (e.g. CpG 1, 2, etc.) with the positions indicated (67, 76, 90, 117, 153, 177, 182, 210, 219, 255, 269, 292, 301, 321, 338, 370, 375, 388, 392, and 412, corresponding to CpG 3, 4, . . . etc.), and the columns correspond to the cell types as analyzed. The abbreviations at the bottom indicate BLC25=B-lymphocytes; CTL01=CD8+ cytotoxic T-cells; GRC52=granulocytes; MOC26=CD14+ monocytes; NKC15=CD56+ NK-cells; and THC14=CD4+ Helper T-cells, respectively.

For the actual epigenetic profiling of the amplicon region in blood cell subtypes, the immune cell populations as analyzed were as follows (see FIG. 1)

BLC25=B-lymphocytes
CTL01=CD8+ cytotoxic T-cells
GRC52=granulocytes
MOC26=CD14+ monocytes
NKC=CD56+ NK-cells
NKT=CD56+CD3+ NKT-cells
THC14=CD4+ Helper T-cells The bisulfite-converted target-regions of preferred qPCR-assay-system as developed were:

```
TpG-specific (SEQ ID NO: 2):
GGTGTGGGTTTGAGTTTATTTTATAGGGTAGGTTTTTGATTATTAGAAGGTGTTATTGTTTTTATTTGGGATAGA

TGTATATTTTTATATGTTTTTAGATATTTTTAAATGGGAGGTGTTTTTTATATTGAGAATAAGATATTATGAAAA

TATGGGAGGGAAGAAATTAATAGTTTTGGGGTGTAAGGAGGTTGGGTTAAGTTGTGTATTGAGGAGGGTGTATAT

GGGGGTTTTGTGGTATTTTTATAGAGTAGTGTAGGGGAAGAGGTGGTTTAGGGTTAAGTTGTGTATTGAGGAGGG

TGTATATGGGGGTTTTGTGGTGTTAAGATGTAGTTGTTGGATTTTATTTAAGAAAAGATATTTAATTGTTGGGGT

GGGGTTAATATTTGGTTGGTTTTGATTGGTTTTAATTTGTTTTAGTAAGAAGGAAATTAGGGGTT

CpG-specific: (SEQ ID NO: 3):
GGTGTGGGTTTGAGTTTATTTTATAGGGTAGGTTTTTGATTATTAGAAGGTGTTATTGTTTTTATTCGGGATAGA

CGTATATTTTTATACGTTTTTAGATATTTTTAAATGGGAGGCGTTTTTTATATTGAGAATAAGATATTATGAAAA

TACGGGAGGGAAGAAATTAATAGTTTCGGGGCGTAAGGAGGTTGGGTTAAGTTGTGTATCGAGGAGGGCGTATAT

GGGGGTTTTGTGGTATTTTTATAGAGTAGCGTAGGGGAAGAGGCGGTTTAGGGTTAAGTTGTGTATCGAGGAGGG

CGTATATGGGGGTTTTGTGGCGTTAAGATGTAGTTGTCGGATTTTATTTAAGAAAAGATATTTAATTGTCGGGGC

GGGGTTAATATTCGGTCGGTTTTGATTGGTTTTAATTCGTTTTAGTAAGAAGGAAATTAGGGGTT
```

The respective sequence of the assay-target region is underlined.

The following primers and probe were used for the qPCR:

| | | |
|---|---|---|
| Forward amplification primer | 2674r | GGTGTGGGTTTGAGTTTATTT (SEQ ID NO: 4) |
| Reverse amplification primer | 2674q | AACCCCTAATTTCCTTCTTACT (SEQ ID NO: 5) |
| Forward primer TpG-specific | 2674r_T_fw | GTTTTGTGGTATTTTTATAGAGTAGT (SEQ ID NO: 6) |

| | | |
|---|---|---|
| Reverse primer TpG-specific | 2674q_T_rev | AGATGGGATGGAATGGTTGT (SEQ ID NO: 7) |
| Probe TpG-specific | 2674_TP | CCTAAACCACCTCTTCCCCTACA (SEQ ID NO: 8) |
| Forward primer CpG-specific | 2674r_C_fw | TTTTGTGGTATTTTTATAGAGTAGC (SEQ ID NO: 9) |
| Reverse primer CpG-specific | 2674q_C_rev | CCATATACGCCCTCCTCG (SEQ ID NO: 10) |
| Probe CpG-specific | 2674_CP | AAACCGCCTCTTCCCCTACG (SEQ ID NO: 11) |

Figure 2A:
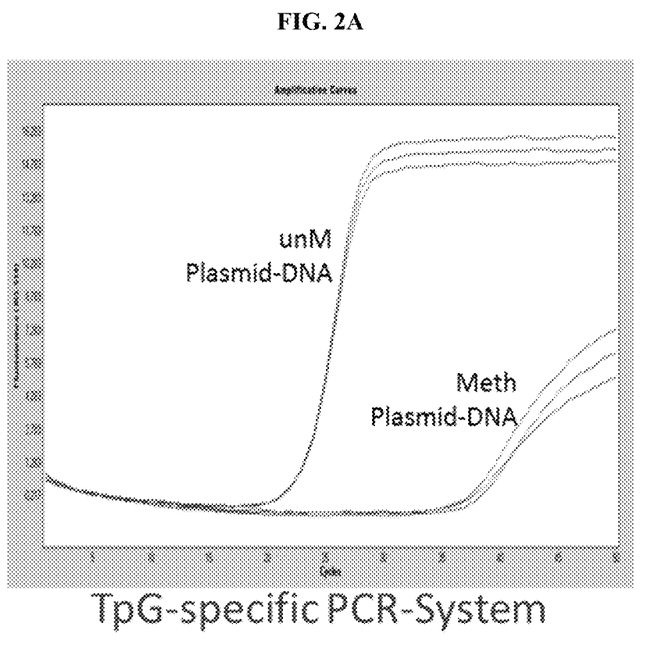
Figure 2B:
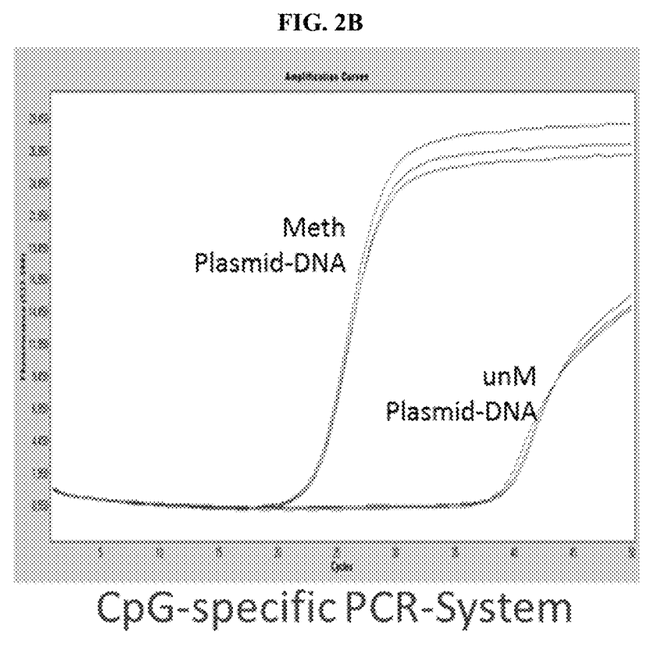

The specificity of the TpG-specific PCR-system was demonstrated using test-templates (plasmid-DNA) as shown in FIGS. 2A-2B.

The cell type specificity (as measured by qPCR) was found as follows:

| Type of immune cell | qPCR-Detection [%] |
|---|---|
| CD56+ NK-cells | 93.29 |
| CD56+CD3+ NK T-cells | 8.94 |
| CD56++ NK-cells ("bright") | 1.43 |
| B-cells | 0.46 |
| CD14+ monocytes | 0.28 |
| CD8+ T-cells | 1.75 |
| CD4+ T-cells | 0.24 |
| CD15+ granulocytes | 0.33 |

The invention claimed is:

1. A method of producing and detecting an amplicon from a bisulfite treated human mevalonate diphosphate decarboxylase (MVD) gene, the method comprising: (a) bisulfite treating human genomic DNA from a sample comprising human immune cells to convert unmethylated cytosines to uracils; (b) amplifying a region of the human MVD gene from the bisulfite treated DNA using methylation specific primers to produce an amplicon comprising thymine-guanine (TG) at TG positions 255 and 269 of SEQ ID NO: 2- and c) detecting the amplicon with a probe comprising the nucleic acid sequence of SEQ ID NO: 8.

2. The method according to claim 1, wherein the TG are detected by a method selected from a methylation specific enzymatic digest, bisulfite sequencing, promoter methylation analysis, CpG island methylation analysis, methylation-specific PCR (MSP), quantitative polymerase chain reaction (qPCR) assay, methylation-sensitive single-nucleotide primer extension (MsSNuPE), and other methods relying on a detection of amplified DNA.

3. The method according to claim 1, further comprising comparing a relative amount of a methylation frequency in the region of the human MVD gene with relative amounts of a methylation frequency in a human control gene.

4. The method according to claim 1, wherein said sample is selected from blood, a tissue, or an organ.

5. The method according to claim 1, wherein said method is performed without a step of purifying and/or enriching said human immune cells.

6. The method according to claim 1, wherein said human suffers from or is likely to suffer from an autoimmune disease, transplant rejection, infection disease, cancer, and/or allergy.

7. The method of claim 1 performed using a kit comprising a) a bisulfite reagent, and b) materials for the analysis of the methylation status of CpG positions selected from the CpG positions in the region according to SEQ ID NO: 1.

8. The method according to claim 1, wherein the amplifying comprises using an oligomer according to any of SEQ ID NOs: 4-7 or 9-11.

9. The method according to claim 3, wherein the control gene is human glyceraldehyde 3-phosphate dehydrogenase (GAPDH).

10. The method according to claim 5, wherein the sample is whole blood and/or non-trypsinized tissue.

11. The method according to claim 1, wherein the human genomic DNA is from a blood sample.

12. The method according to claim 1, further comprising
d) detecting a methylation status of cytosine-phosphate-guanine (CpG) positions from the amplicon.

13. A method of producing and detecting an amplicon from a human mevalonate diphosphate decarboxylase (MVD) gene, the method comprising: (a) bisulfite treating DNA from a human sample to generate bisulfite treated DNA where unmethylated cytosines are converted to uracils, (b) amplifying with polymerase chain reaction (PCR) a region of the bisulfite treated DNA corresponding to a human mevalonate diphosphate decarboxylase (MVD) gene to produce the amplicon from the bisulfite treated DNA, and c) detecting the amplicon with a probe comprising the nucleic acid sequence of SEQ ID NO: 8, wherein the PCR is performed with methylation specific primers that amplify SEQ ID NO: 2.

14. The method of claim 13, wherein the sample is a blood sample.

15. The method of claim 13, further comprising
d) detecting a methylation status of at least one cytosine-phosphate-guanine (CpG) position of SEQ ID NO: 1 from the amplicon.

16. The method of claim 1, wherein the amplicon comprises SEQ ID NO: 2.

17. The method of claim 1, wherein the step of amplifying uses methylation specific primers that amplify SEQ ID NO: 2.

18. The method of claim 13, wherein the amplicon comprises SEQ ID NO: 2.

* * * * *